(12) United States Patent
Calder

(10) Patent No.: US 11,910,779 B2
(45) Date of Patent: Feb. 27, 2024

(54) ANIMAL MARKING AND INOCULATION

(71) Applicant: Simcro Limited, Hamilton (NZ)

(72) Inventor: David Calder, Hamilton (NZ)

(73) Assignee: Datamars SA, Lamone (CH)

( * ) Notice: Subject to any disclaimer, the term of this patent is extended or adjusted under 35 U.S.C. 154(b) by 0 days.

(21) Appl. No.: 16/052,103

(22) Filed: Aug. 1, 2018

(65) Prior Publication Data
US 2019/0037804 A1 Feb. 7, 2019

Related U.S. Application Data

(60) Provisional application No. 62/540,023, filed on Aug. 1, 2017.

(51) Int. Cl.
*A01K 11/00* (2006.01)
*A01K 67/027* (2006.01)

(52) U.S. Cl.
CPC .......... *A01K 11/005* (2013.01); *A01K 67/027* (2013.01); *A01K 2207/00* (2013.01)

(58) Field of Classification Search
CPC ... A01K 11/00; A01K 11/005; A61M 37/0076
See application file for complete search history.

(56) References Cited

U.S. PATENT DOCUMENTS

| | | | | |
|---|---|---|---|---|
| 6,482,187 B1 * | 11/2002 | Gibbs | ...................... | A61D 7/00 604/130 |
| 6,527,750 B1 * | 3/2003 | Frandsen | ................. | A61D 7/00 606/116 |
| 2001/0037124 A1 * | 11/2001 | Matera, Jr. | ........... | A01K 11/005 606/186 |
| 2004/0220527 A1 * | 11/2004 | Buckley | ................. | A01K 11/00 604/191 |

FOREIGN PATENT DOCUMENTS

WO  WO-9428709 A1 * 12/1994 .......... A01K 13/003

* cited by examiner

*Primary Examiner* — Kelly J Bekker
*Assistant Examiner* — Mohammed S Adam
(74) *Attorney, Agent, or Firm* — Lowe Graham Jones PLLC

(57) ABSTRACT

The invention is directed to an animal marking and treatment apparatus. The marking apparatus is an animal treatment apparatus to apply an animal treatment to a surface or subcutaneous layer of an animal via an operative end. The marking apparatus includes a marking portion, attached to the animal treatment apparatus, and located at the operative end. The marking apparatus is located such that when the animal receives the treatment the marking portion marks the animal by stamping at the same time.

13 Claims, 12 Drawing Sheets

ANIMAL MARKING AND INOCULATION

PRIORITY CLAIM

This application claims the benefit of prior U.S. provisional application Ser. No. 62/540,023, filed Aug. 1, 2017.

FIELD OF THE INVENTION

The present invention relates to methods and apparatus for marking and inoculating animals.

In particular, though not solely, the present invention is directed to methods and apparatus that inoculate, or otherwise inject or treat an animal with a medicament that then also mark the animal as having been inoculated.

BACKGROUND OF THE INVENTION

There is a need when dealing with animals to mark them. This need may arise for a number of reasons, but a primary one is to show if that animal has received a treatment or not. Normally such markings are some form of color applied to an exterior of the animal, such as the head, side, or hindquarters, that is visible from a distance or close up and indicates the animal has received the treatment.

One such solution that exists is the use of a crayon or paint stick marker to place a mark on the animal after it has been treated. This is usually placed in an area on the animal that provides good visibility to the operator to indicate to the operator or to other people that the animal has received a treatment. The marker is hand-held and can be carried and used by the operator as a secondary activity to the treatment, or carried and used by another person, also as a secondary activity to the treatment. In some cases, the marker is directly mounted to the treatment device, and so the marking can be made by the operator. However, the marker is fixed to one portion of the treatment device and requires a secondary operation immediately after the treatment. For example after spraying with the treatment the operator turns the treatment device, for example a drench gun, around to where the crayon is located and then marks the animal by drawing the needed mark.

One such crayon or marker of the prior art is that sold under the name Raidex Animal Marking Crayon. This may be handled, or in some way, often contrived by the user, mounted to the treatment apparatus, for example by using a zip tie or similar. The disadvantage of such a system is that it requires the operator, once they have applied the treatment, to then perform the secondary operation of marking the animal, either by hand, or using the treatment apparatus. This requirement of the secondary operation is a burden on the operator, as it requires them to perform two operations, both separate. This becomes a problem when there are large numbers of animals to treat and mark, the repetitive nature of performing both tasks separately can place a strain on the user's hands and result in injury. Further performing two separate operations increases the overall time of the operation. Worse still this method requires the operator, or second operator, to remember to mark the animal. Therefore, it is prone to error and possible non-marking of the animal despite being treated. This can lead to the animal being treated again. Alternatively, animals may be marked that have not been treated. This can result in the animal being untreated, which may make it unhealthy.

A further solution is a pressurized paint cartridge directly mounted to the treatment device and as the treatment is being made to the animal, a spray of paint is discharged from the cartridge to mark the animal. The paint spray is made near the site of the treatment. There are a number of challenges with this device based on external market research in the USA. The paint cartridge valve can stick open causing excess paint to be discharged and users to stop treatment to remedy the situation. This causes undue delay, and wastage of the marking paint and a mess. The paint spray propellant is usually solvent based and the unpleasant odor can readily contaminate the immediate environment the operator is working in. This is particularly evident when animals are treated in closed environments especially in winter months. The pressurized spray system typically administers 100-150 discharges and therefore the user is required to change out the paint cartridge frequently in larger operations. There is the potential for the operator to hold the trigger down for extended periods of time when treating a squirming animal resulting in excess use of paint and excess spray on the animal and/or its surrounds. The paint spray has a relatively wide spray pattern and the paint droplets may not be particularly uniform in size nor well dispersed. Overspray is common, and in some cases, the paint spray may disperse over and potentially visually obliterate or contaminate the injection treatment site. For at least these reasons such a pressurized system is undesirable.

Also present systems, particularly those where there are two operators, do not automatically identify the location on the surface of the animal where the treatment was applied. Up until now marking of the animal has served only to identify which animals were treated. However there is a growing need to also note where on the animal a treatment has been applied. Either to prevent that part entering the food chain, or to ensure other treatments are not applied in the same location.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

It is an object of the present invention to provide improved marking and inoculation methods and apparatus or to overcome the above shortcomings or address the above desiderata, or to provide an improved marking and inoculation method and apparatus that safeguards, or reduces the risk to, the user from needle stick, while also increasing the confidence in marking of the animal indicating a successful inoculation, or to at least provide the public with a useful choice.

SUMMARY OF THE INVENTION

In a first aspect the present invention may be said to broadly consist in an animal marking and treatment apparatus, comprising or including, an animal treatment apparatus to apply an animal treatment to a surface or subcutaneous layer of an animal via an operative end, and a marking portion, attached to the animal treatment apparatus, and located at the operative end, such that when the animal receives the treatment the marking portion marks the animal by stamping at the same time.

Preferably the apparatus requires no additional movement or operation from the operator to stamp the mark over the movement or operation of treating the animal.

Preferably the marking also marks the location of where the treatment was applied.

Preferably the marking portion is an absorbent pad that contains a marking medium, such as an ink or paint.

Preferably the marking portion is circular and is capable of leaving a circular mark on the animal.

Preferably the animal treatment is applied through a hollow center of the marking portion.

Alternatively the animal treatment is applied outside the periphery of the marking portion.

Preferably the marking portion includes a housing that holds and presents the absorbent pad to the animal for marking when in use Preferably the housing has a mounting portion, at an opposing end to that holding the absorbent pad, to co-operate with a mount on the operative end of the treatment apparatus.

Preferably the housing holding the absorbent pad and the mounting portion form a cassette that can be attached and removed from the treatment apparatus.

Preferably the marking medium is an odorless, food contact approved ink.

Preferably the absorbent pad can be refilled with marking medium, either in place on the treatment apparatus, or when removed from the treatment apparatus.

Alternatively the cassette is supplied as a non-serviceable consumable part that can be easily swapped out by the operator without any mess or clean-up process when the pre-stamped ink pad is exhausted.

Preferably there is an offset bracket to attach to the mount and to which the mounting portion can attach to offset the marking portion when the animal treatment is applied outside the periphery of the marking portion Preferably the offset bracket places the marking portion at the desired angle to the surface or subcutaneous layer.

Preferably the offset bracket is angled to apply the mark to a surface that is not on the same plane as that where the treatment is applied, for example where the animal surface is curved, such as a next, leg, side or similar.

Preferably the cassette includes a removable cover for the absorbent pad to prevent it drying out.

Preferably the cassette forms a needle guard that covers a needle of the treatment apparatus save for when the treatment apparatus is applied to the surface of the animal.

Preferably the cover can be replaced on, or over, the absorbent pad when marking is not desired or when the treatment apparatus is not in use.

Preferably the mark when circular encircles the location of the surface where the treatment was applied.

In another aspect the present invention may be said to broadly consist in a marking cassette for attachment to an animal treatment apparatus, comprising or including, a housing that has a holding portion at one end, and a mounting portion to engage directly or indirectly, to an animal treatment apparatus at an opposing end, a marking portion located in the holding portion, the marking portion adapted to mark a surface of an animal when applied thereto and leave at least a portion of a circular mark on the surface, and a cover to cover the marking portion, wherein the cassette when mounted to a treatment apparatus will, in use, leave a mark on an animal indicating the treatment has been applied, and the location of the treatment.

Preferably the marking portion consists of an absorbent pad that contains a marking medium such as ink or paint.

Preferably the housing is circular with a hollow center through which the treatment is applied.

Preferably the absorbent pad is refillable from a separate supply of marking medium, whether the cassette is mounted to the treatment apparatus, or removed therefrom.

In another aspect the present invention may be said to broadly consist in a method of marking and treating an animal, comprising or including the steps of, applying a treatment apparatus to, or near a surface of an animal, triggering the treatment apparatus to apply a treatment to the surface or subcutaneous layer thereof, marking the animal at or adjacent the site of the treatment from a marking portion mounted to the treatment apparatus as part of the step of applying the treatment apparatus to the animal, such that the animal is treated and marked as being treated, and the location of the treatment in the one motion.

In another aspect the present invention may be said to broadly consist in a kit of parts for marking an animal, comprising or including, a cassette including a marking portion and a mounting portion for mounting to an animal treatment apparatus, a supply of marking medium for application to the marking portion, such that when the cassette is mounted to the treatment apparatus it can mark an animal as being treated and the location of the treatment in one movement or step.

Preferably the kit includes a cover for the marking portion.

Preferably the kit includes a plurality of cassettes, such that when one cassette runs out of marking portion, it can be removed and replaced by another, and refilled at a later point in time.

Preferably the kit includes an offset bracket to offset the cassette relative to the treatment location, for example to enable marking on a surface that is in a differing plane or place to that of the treatment location.

In another aspect the present invention may be said to broadly consist in a marking cassette as described herein with reference to any one or more of the accompanying drawings.

In another aspect the present invention may be said to broadly consist in an animal marking and treatment apparatus as described herein with reference to any one or more of the accompanying drawings.

In another aspect the present invention may be said to broadly consist in a method of marking and treating an animal as described herein with reference to any one or more of the accompanying drawings.

In another aspect the present invention may be said to broadly consist in a kit of parts for marking an animal as described herein with reference to any one or more of the accompanying drawings.

As used herein the term "and/or" means "and" or "or", or both.

As used herein "(s)" following a noun means the plural and/or singular forms of the noun.

The term "comprising" as used in this specification means "consisting at least in part of". When interpreting statements in this specification which include that term, the features, prefaced by that term in each statement, all need to be present, but other features can also be present. Related terms such as "comprise" and "comprised" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

The entire disclosures of all applications, patents and publications, cited above and below, if any, are hereby incorporated by reference.

This invention may also be said broadly to consist in the parts, elements and features referred to or indicated in the specification of the application, individually or collectively, and any or all combinations of any two or more of said parts, elements and features, and where specific integers are mentioned herein which have known equivalents in the art to which this invention relates, such known equivalents are deemed to be incorporated herein as if individually set forth.

Other aspects of the invention may become apparent from the following description which is given by way of example only and with reference to the accompanying drawings.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

Shown in FIGS. 1 through 7 is the marking cassette 16 in keeping with the present invention attached to a treatment apparatus 2 and on its own, and marking 7 on an animal 4.

Figure 1:
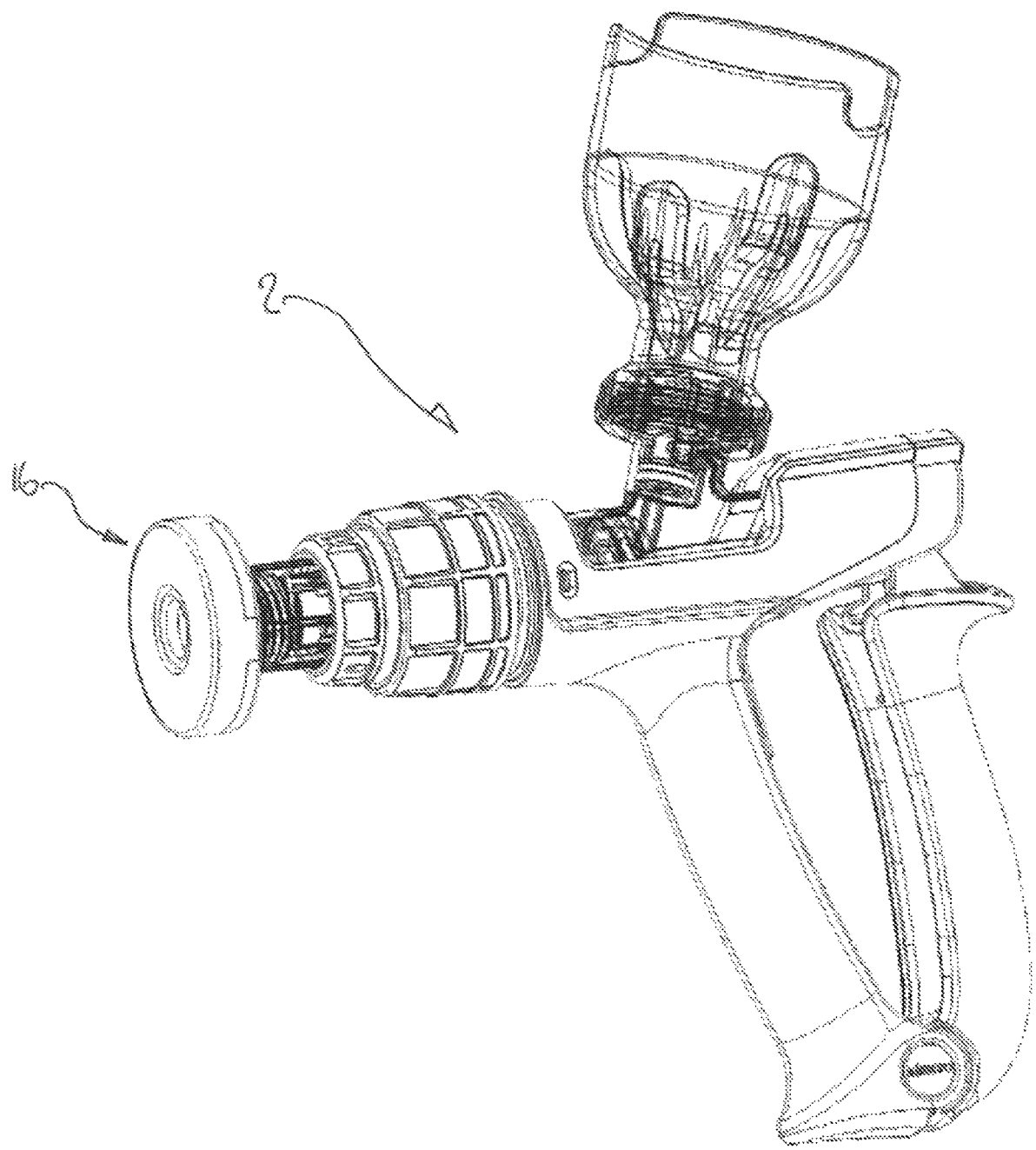
FIG. 1 shows an isometric view of a treatment apparatus with the marking cassette attached at the operative end.
Figure 2:
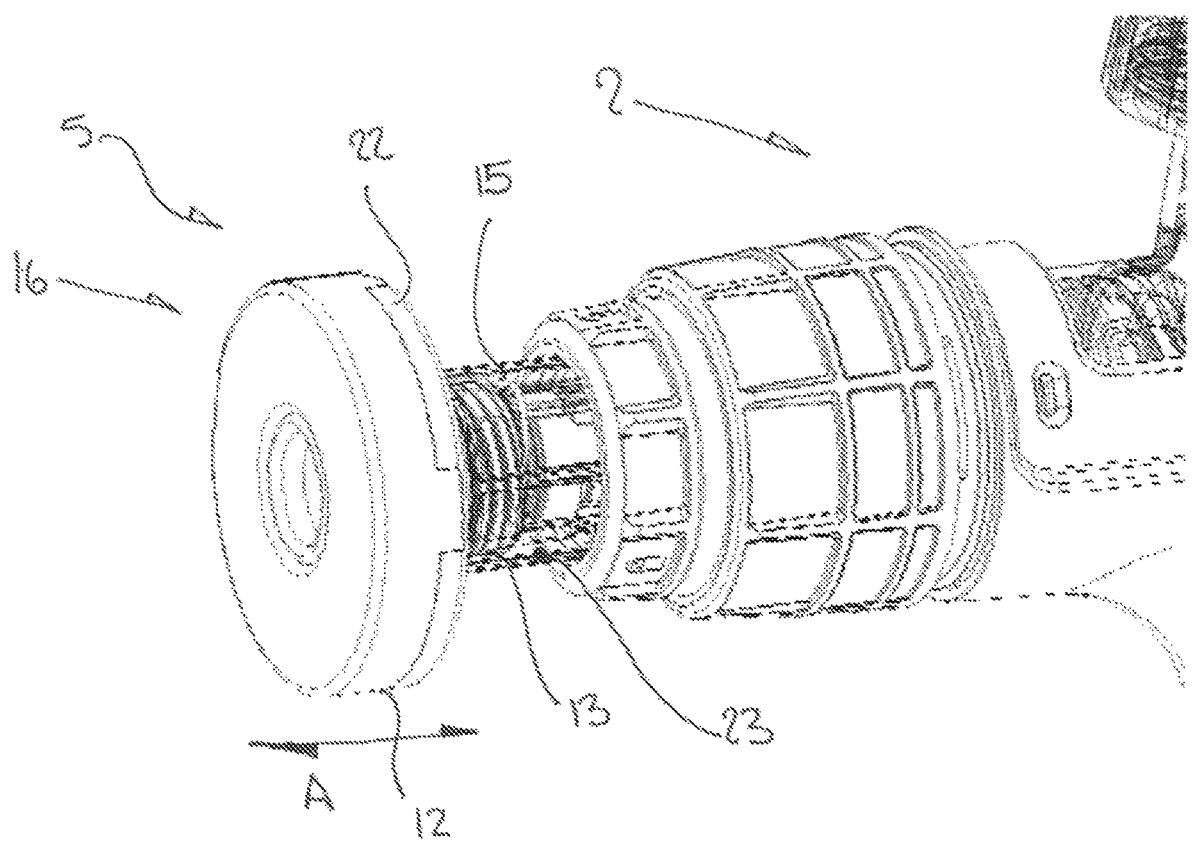
FIG. 2 shows a close up of the marking cassette from FIG. 1.
Figure 3:
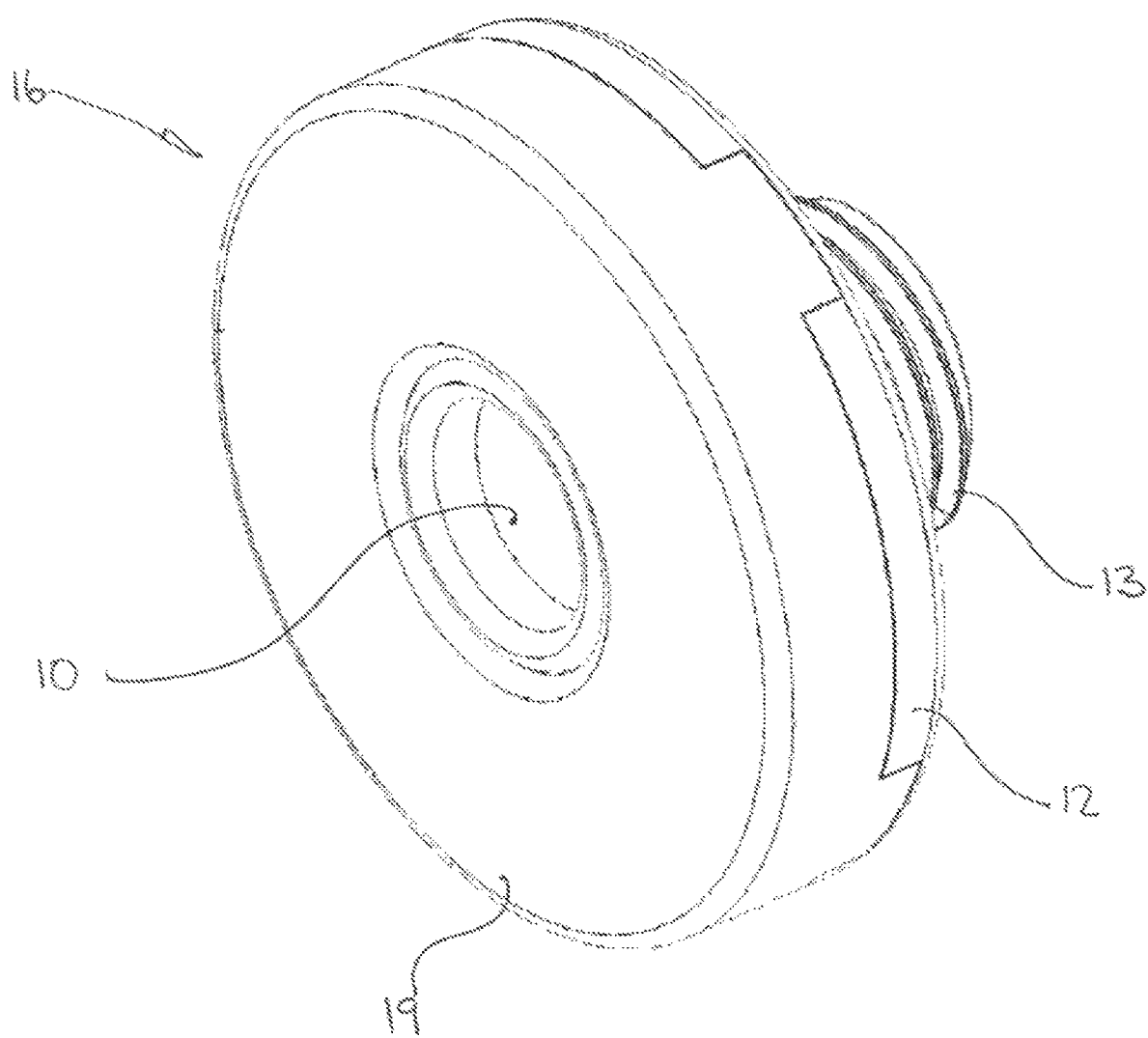
FIG. 3 shows an isometric front view of the marking cassette.
Figure 4:
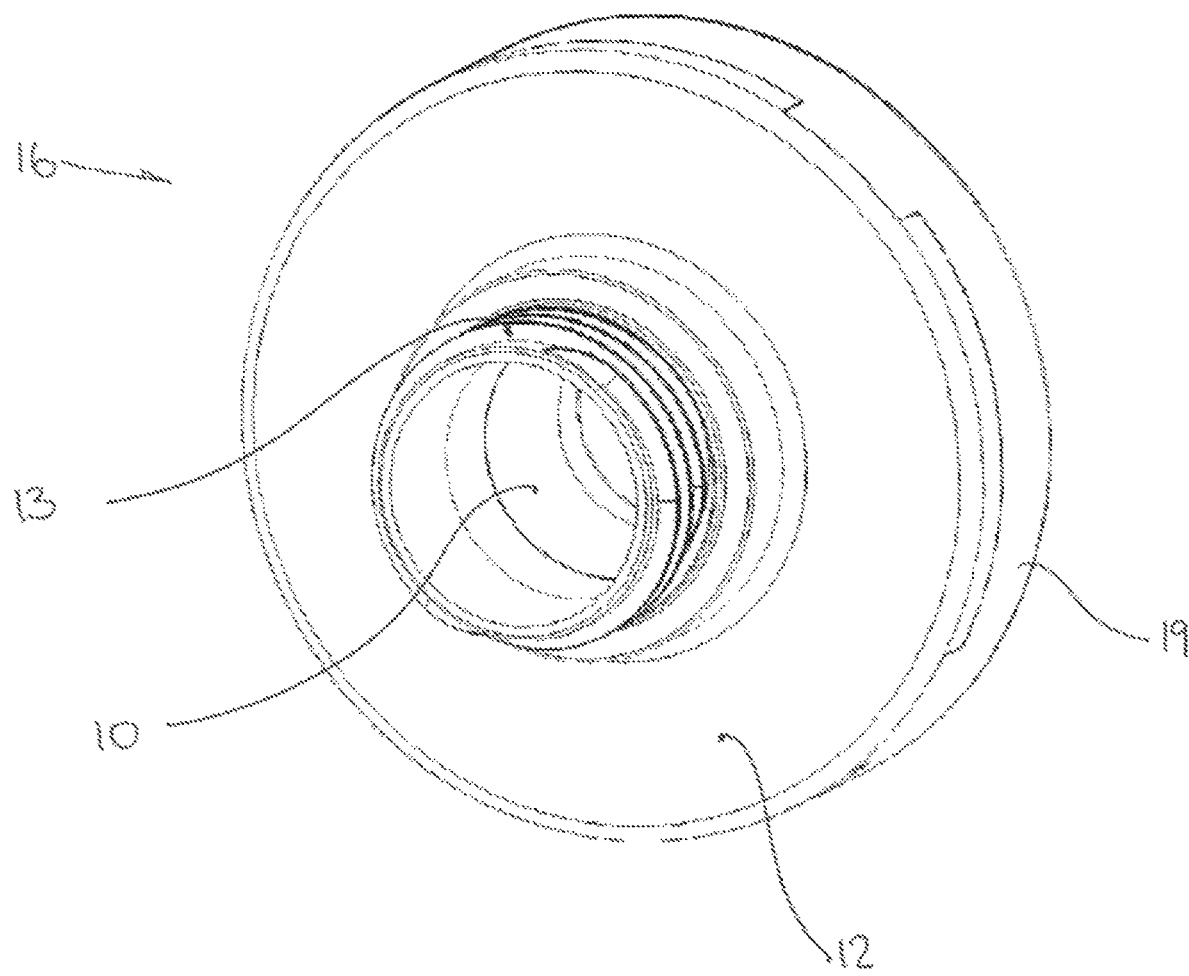
FIG. 4 shows an isometric rear view of the marking cassette of FIG. 3.

The marking cassette 16, shown generally in FIG. 1 and in detail in FIGS. 2 through 4, consists of a housing 12 which has a holding portion 22 which houses or forms a marking portion 6 and the housing also has a mounting portion 13. In the embodiment shown the mounting portion 13 is a threaded engagement to a complimentary mount 15 of the operative end 5 treatment apparatus 2. However, it could be any form of engagement as desired such as a press or push fit, a bayonet fitting or any other form that will sufficiently engage the cassette 16 to the apparatus 2. The treatment apparatus 2 shown is a needle 18 (not shown in those Figures, but visible in FIG. 8) type apparatus for subcutaneous delivery, however it may also be any other form of treatment apparatus, whether subcutaneous, intra-orifice (for example, nasal, oral or otherwise) or surface.

In the embodiment shown in FIG. 1 the marking cassette 16 is mounted to a sliding portion 23 of the treatment apparatus 2. The sliding portion can slide along the major axis of the apparatus, back and forth in the direction A as shown in FIG. 2. The sliding portion 23 by itself, or in conjunction with the marking cassette 16 forms a needle guard that covers the needle 18 until the treatment apparatus 2 is pressed against the animal 4. In FIG. 2 the needle guard functionality is shown being active such that it is guarding the needle 18 and therefore the needle cannot be seen. However the needle 18 would extend out the hollow center 10 in the embodiment shown in FIGS. 1 to 4. When pressed against the animal 4 the needle 18 is allowed to extend past the end of the marking cassette 16 to apply the treatment, and the marking cassette 16 can apply the mark 7. When the treatment apparatus 2 is removed from the animal 4, the sliding portion 23, under bias, extends and the needle 18 is then covered again. The sliding portion 23 may cover the needle 18 entirely by itself when extended to the tip 24 of the needle 18, or may rely on the additional length of the marking cassette 16 to provide the full length to cover the needle 18. If the sliding portion is long enough by itself then this provides additional safety of covering the needle even if the marking cassette 16 is removed, for example when changing the marking cassette 16, or using the treatment apparatus with the marking cassette 16 removed.

The length of the marking cassette 16 axially may also vary to allow variation of the depth of penetration of the needle 18.

Figure 9:
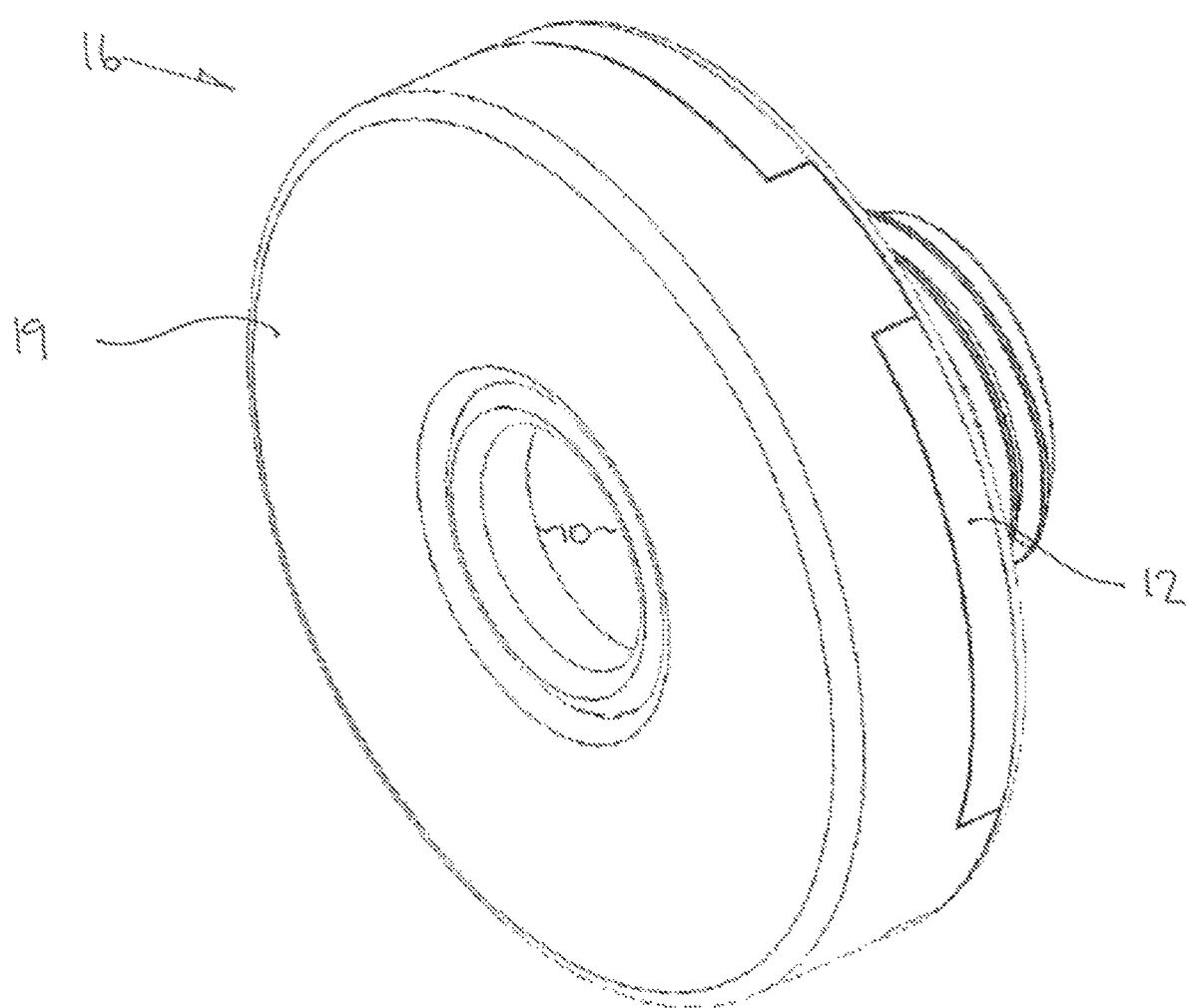
FIG. 9 is an isometric view of the cassette with cover clipped to the housing.
Figure 10:
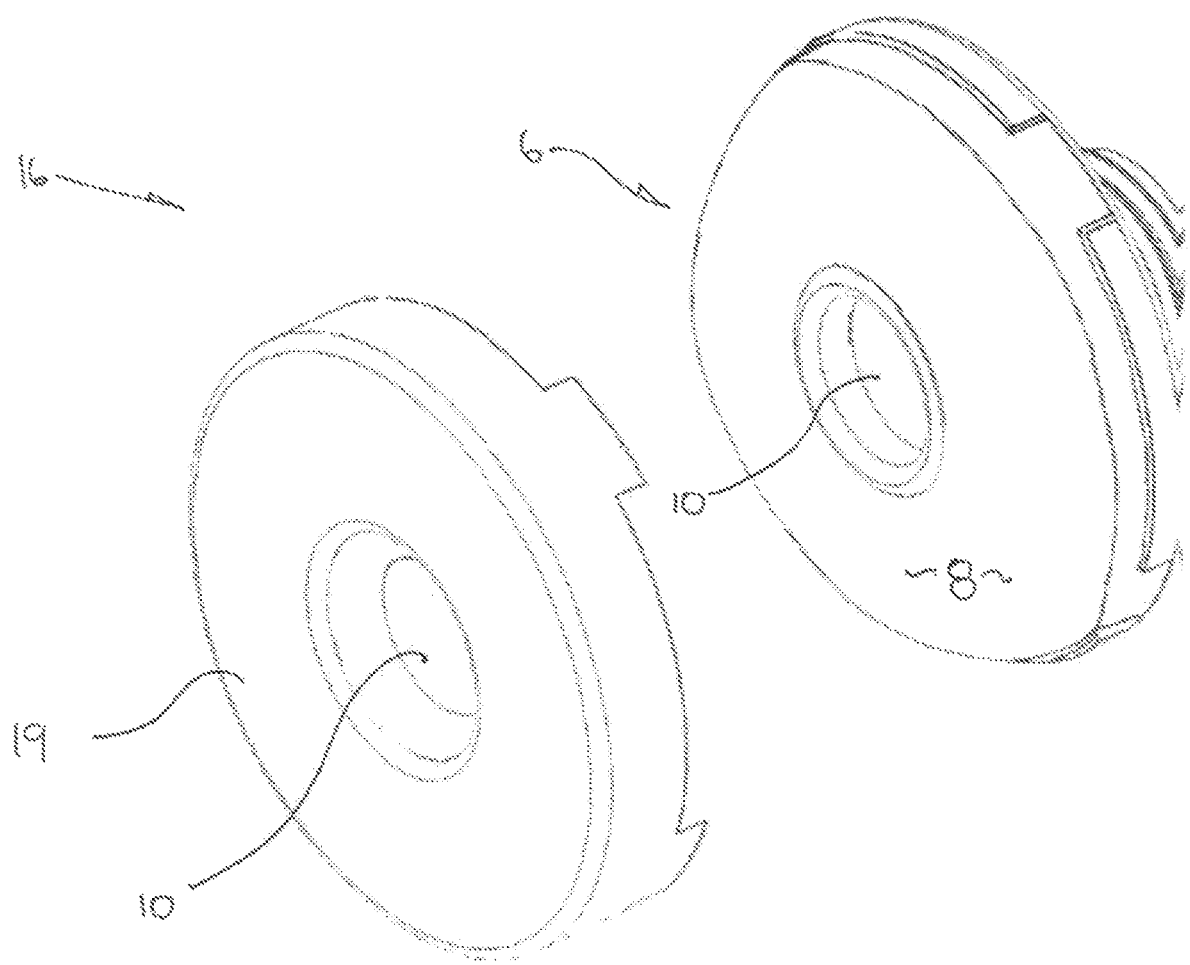
FIG. 10 is a similar view to FIG. 9 with the cover unclipped from the housing to expose the marking portion.
Figure 11A:
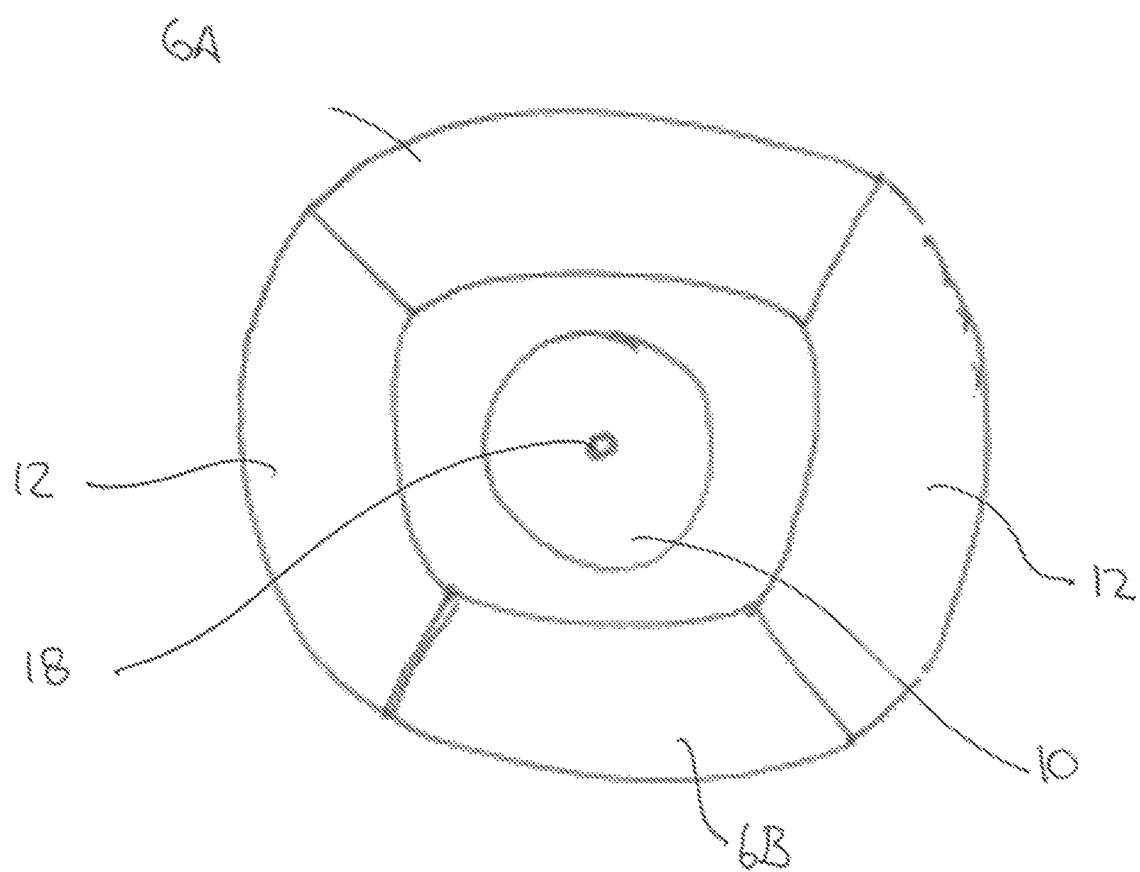
FIG. 11A shows a variation in the cassette to have a differing shaped marking portion or portions, whether fully enclosing or open around the needle, and whether having differing colored portions or not.
Figure 11B:
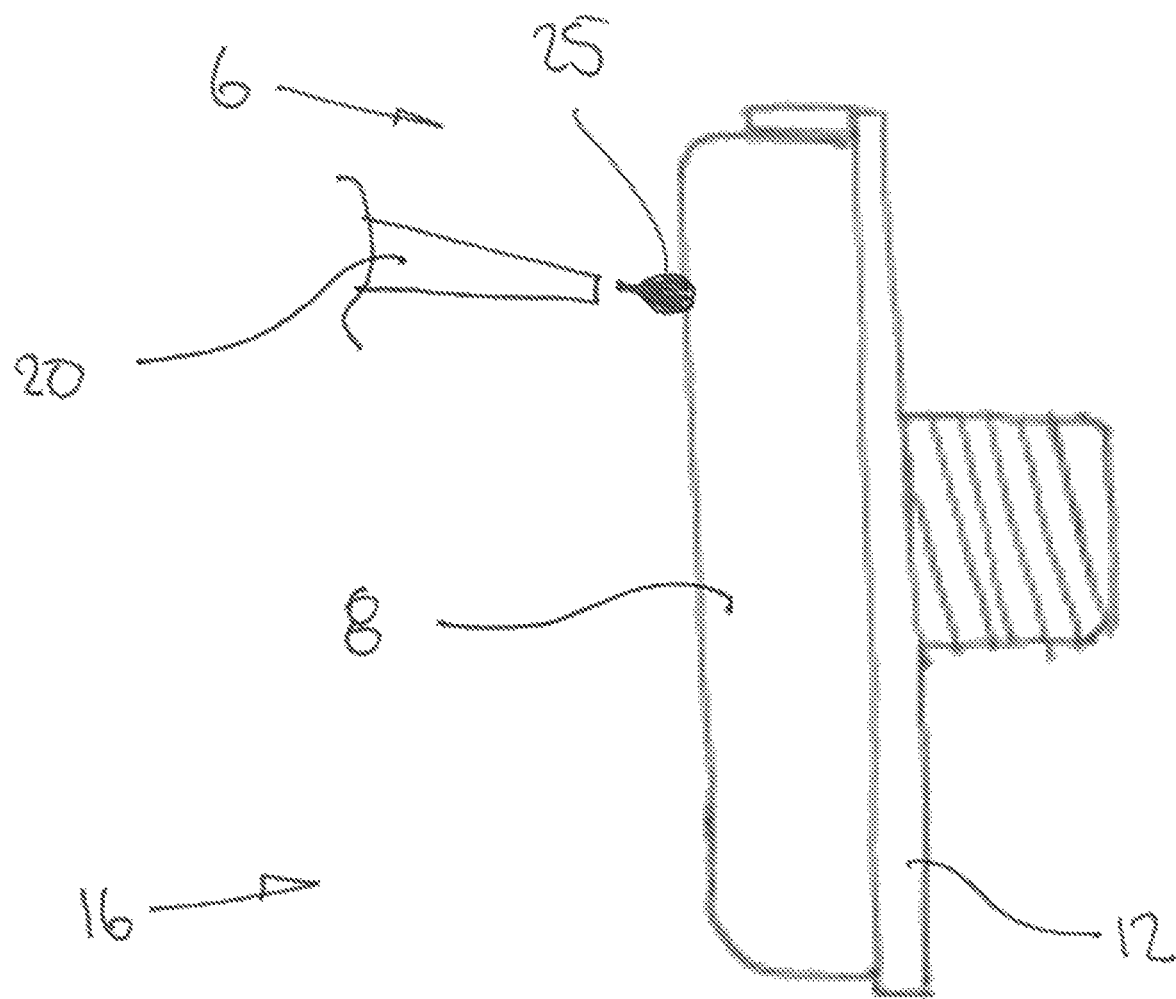
FIG. 11B shows the cassette side on with the cover removed and the marking portion exposed and extending from the housing, and the optional ability to refill the marking portion.

The marking portion 6 can be achieved in a number of ways, but in the preferred form there is an absorbent pad 8 held there, as shown in FIGS. 9 through 11. The absorbent pad 8 contains a marking medium, such as for example an odorless, non-toxic and/or food contact approved ink or similar. The absorbent pad 8 may optionally be covered by a cover 19, which may be replaceable on the pad 8 when not in use, or no marking is desired, or may simply be there initially and is discarded when the cassette 16 is attached. In the embodiment shown in FIG. 10 the cover 19 clips into place on and off the housing 12 to cover the marking portion 6. When clipped to the housing 12 the cover 19 enables the cassette 16 to easily be handled and stored without marking or drying out. Cassettes 16 may be supplied in bulk or as aftermarket in this way to replace used cassettes 19, or place onto treatment apparatus 2 as needed. The cover 19 connection may be sufficient to prevent drying out when in place, or may need an additional seal, for example a tamper evident tear off wrapping.

Figure 6:
FIG. 6 shows a top view of an animal surface after treatment and marking in the one step, with the mark encircling or indicating the treatment location.

In the preferred form the marking portion 6 is sufficient to apply between 100 and 300 marks 7, and experience has shown that a capacity of 150 is preferred. The mark 7 as shown in FIG. 6, on the surface 3 of the animal 4 provides a stable and durable ink that will not drip or contaminate the actual treatment point 21.

The cassette 16 may be reusable. For example when the supply of marking medium 9 runs out in the absorbent pad 8, the cassette 16 may be removed and another fully charged one put in its place. The then removed cassette 16 may then be recharged with ink 25 from a supply of marking medium 20 as is needed as shown in FIG. 11. Alternately if desired the absorbent pad may simply be recharged in situ on the treatment apparatus 2.

The marking portion 6 is as shown in FIGS. 1 through 5 is circular with a hollow center 10. The hollow center 10 allows for concentric mounting on the treatment apparatus 2 about the needle 18, or other treatment application portion of the treatment apparatus 2. The cassette 16 then can also form a needle guard to prevent accidental needle stick by a user to the animal, themselves or other users, until the needle 18 is deployed in the treatment action. The method being that when the treatment apparatus 2 is activated when located against the surface 3 of the animal 4 the needle extends through the hollow center 10 penetrates the skin and delivers the treatment, and at the same time the marking portion 6 applies the mark 7 to the surface 3. While subcutaneous treatment by needle 18 is mentioned here, the treatment may also be topical for example by spraying or squirting on the surface 3, or may be intraorifice, whether oral, nasal or otherwise with a suitable applicator and the cassette 16 and marking portion 6 set at the appropriate distance to apply the mark 7 whether at or near the treatment location. In this way the marking portion 6 will still mark 7 the location 21.

However, the marking portion 6 may be of other forms also, for example an arc or partial circle, or oval or other closed form as shown in FIG. 11A. The marking portion 6 in one form may consist of one 6A or two 6A and 6B marking portions raised above the housing 12, and could include more than one color, whether each separate part is of a differing color, Alternative the marking portion 6 is a single part but has differing color ink portions.

The pre-inked absorbent marker 16 can be supplied as an easily refillable system, as described. Alternatively it can also be supplied as a non-serviceable consumable part that can be easily swapped out by the operator without any mess or clean-up process when the pre-stamped ink pad is exhausted.

With marking 7 concentrically around the treatment site 21 as seen in FIG. 6 the site can be more readily identifiable. This is not the case with current methods and the present invention has advantages for compliance. Not limited to, but including, ensuring the injection site can be identified to encourage correct placement of injection according to certain best practice guidelines, and to identify potential injection site lesions post treatment.

Figure 5:
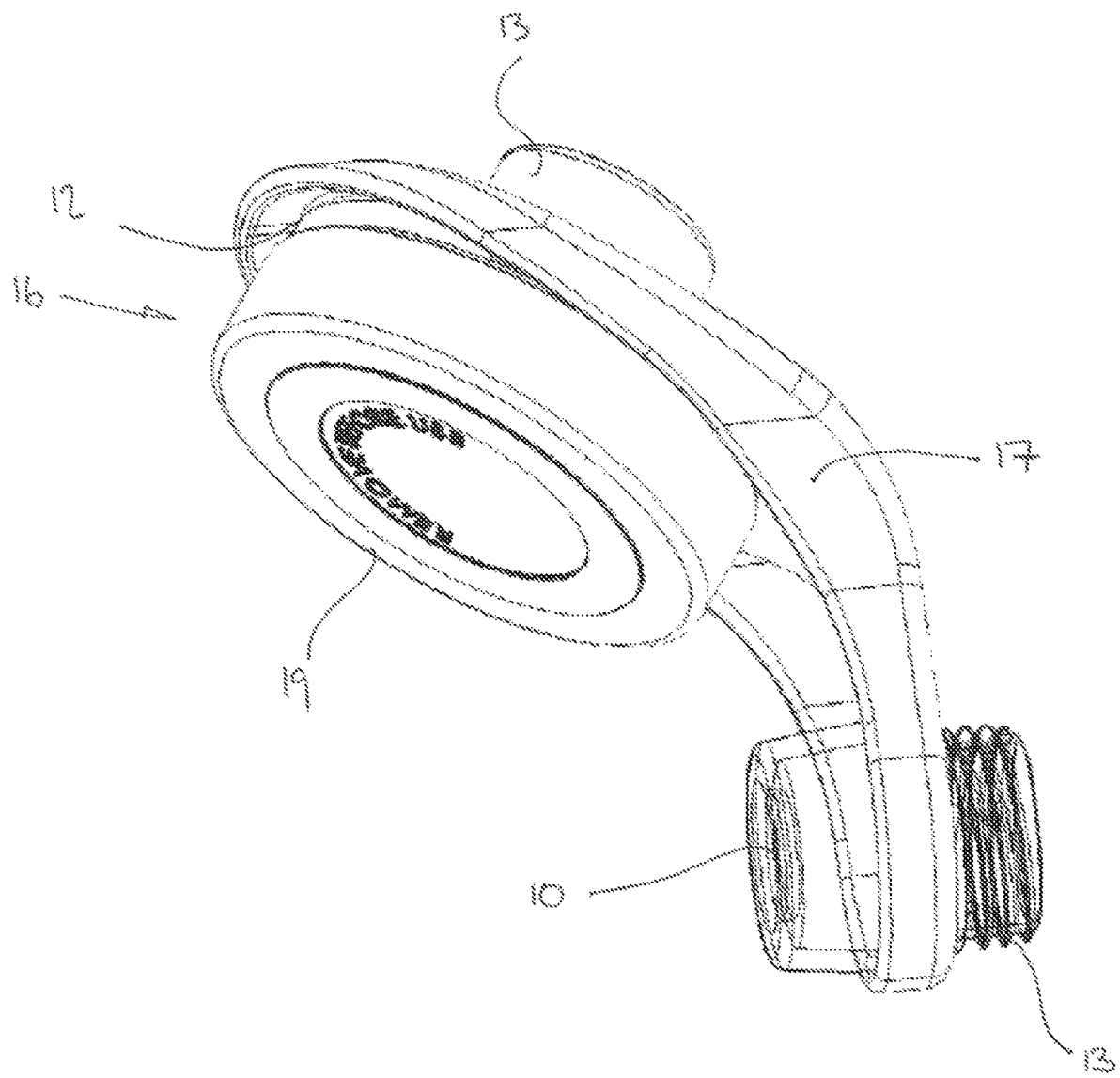
FIG. 5 shows the marking cassette of FIG. 1 with a cover in place and mounted to an offset bracket.
Figure 7:
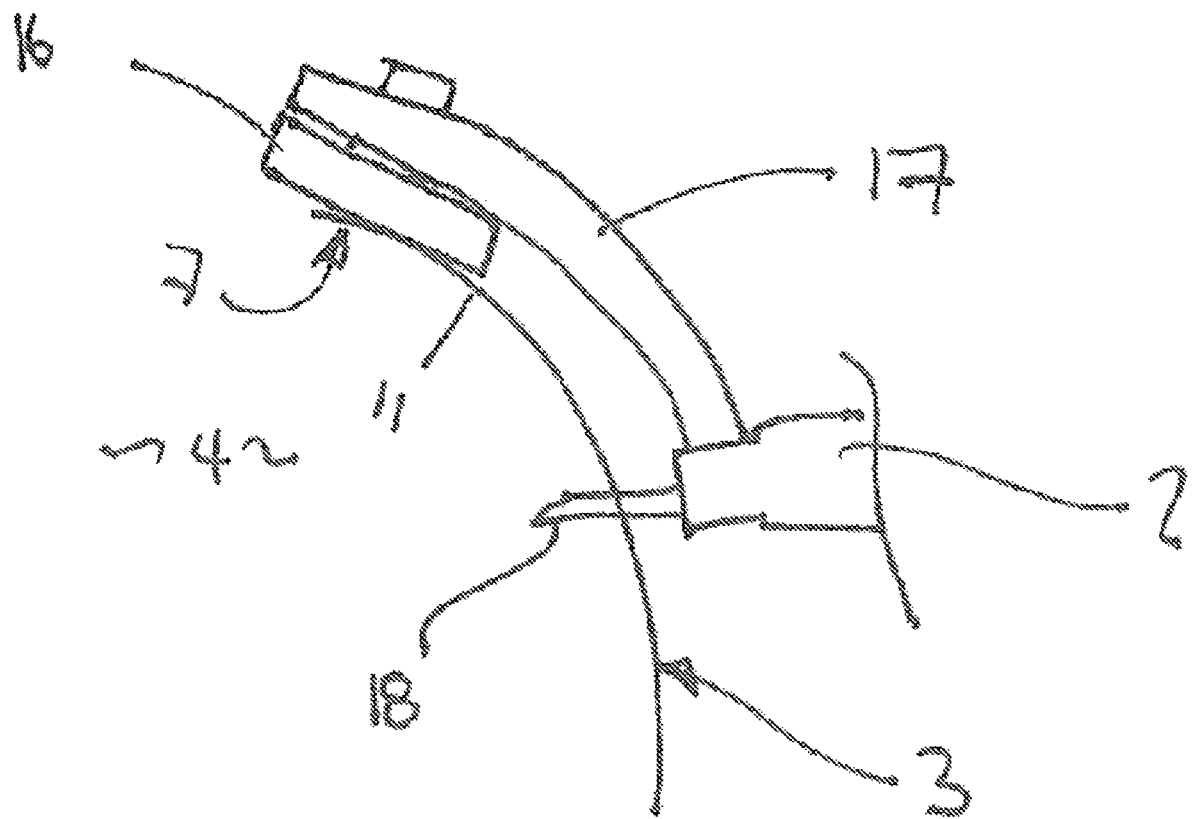
FIG. 7 shows in side view the use of the offset bracket to allows treatment and marking in one step when the surface of the animal is curved, or the treatment location and marking locations are in differing planes.

In some applications the treatment location 21 may be in a differing plane to the location desired for the mark 7, for example outside the periphery 11 of the mark 7. In this case an offset bracket 17 is used as shown in FIGS. 5 and 7. This has a similar mounting portion 13 to the cassette 16, and this mounting portion 13 engages with that of the treatment apparatus 2. The offset bracket 17 then has an angled body as desired (or can be configured or bent as needed) that has a portion that then receives the mounting portion 13 of the cassette 16. In this way as shown in FIG. 7 the location 21 of the treatment is offset to that of the mark 7. This is desirable when the location 21 for example may be in the neck of the animal 4, and it is desirable to see the mark 7 more convenient from above.

Figure 8:
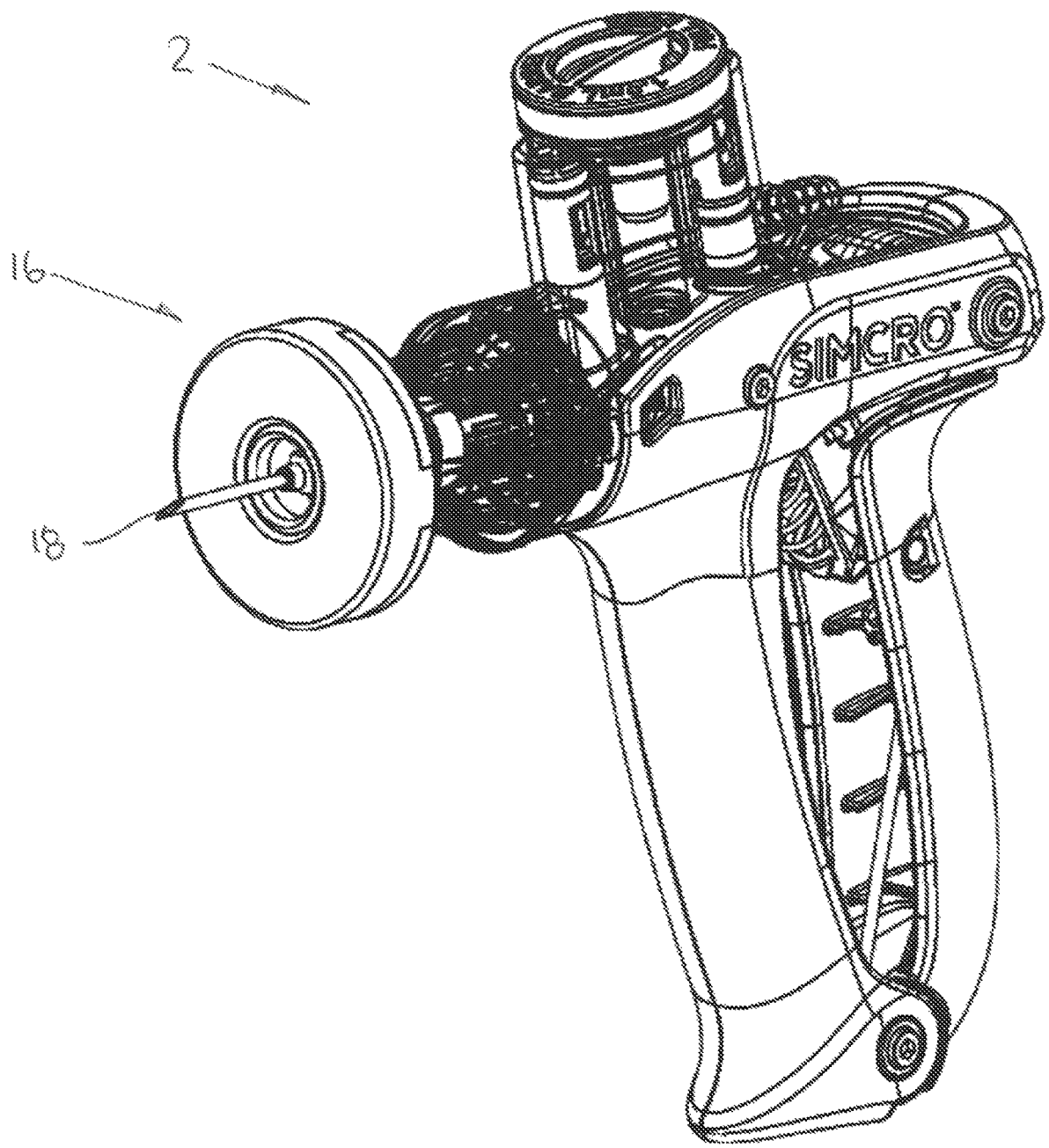
FIG. 8 shows a variation of the system attached to treatment apparatus, where there is no needle guard action and the needle is exposed, or there is a needle guar action, and the needle guard action is slid back to expose the needle.

A further variation of the mount 15 is shown in FIG. 8 where the marking cassette 16 is mounted concentric with the needle 18, but the marking cassette 16 is mounted to the treatment apparatus 2, for example injecting gun, in a way that it does not slide out of the way to expose the needle 18 when injecting. In other words there is no needle guard functionality as it is not connected to a sliding portion 24 as in FIG. 1.

In this variation the marking cassette is the same, or substantially the same as earlier described, however there is no retractable needle guard functionality. The marking cassette 16 is secured stationary via a thread, for example, and acts as a backstop when pressing the needle 18 into the animal 4. This provides additional depth control and prevents the operator pressing the hub of the needle 18 into the injection site potentially causing undue damage to the injection site, potentially resulting in a site reaction (that could lead to infection). The needle 18 always remains in front of the marking cassette 16 so contact of the cassette 16 with the animal 4 only occurs at full needle 18 penetration.

Likewise the position of the marking cassette 16 in FIG. 8 is similar to the location the cassette 16 is in once the sliding portion 23 of the treatment apparatus 2 is pushed back along direction A to expose the needle 18.

The foregoing description of the invention includes preferred forms thereof. Modifications may be made thereto without departing from the scope of the invention.

I claim:

1. An animal marking and treatment apparatus, comprising:
   an animal treatment apparatus to apply an animal treatment to a surface or subcutaneous layer at a treatment location of an animal via an applicator at an operative end, and
   a marking portion, attached to the animal treatment apparatus, and located at the operative end;
   the marking portion is an absorbent pad containing a marking medium, held and presented within a cassette, and the cassette has a mounting portion, at an opposing end to that holding the absorbent pad, to cooperate with a mount on the operative end of the animal treatment apparatus;
   the cassette further being removably attachable to the animal treatment apparatus, and the cassette includes a removably replaceable cover for the absorbent pad to prevent the absorbent pad from drying out, wherein the removably replaceable cover has a proximal end and a distal end, the removably replaceable cover further having a hollow center which extends from the proximal end to and through the distal end;
   the cassette when mounted to the operative end forms at least in part a guard over the applicator at the operative end;
   wherein the marking portion has a hollow center corresponding at least in part with the hollow center of the removably replaceable cover and is configured to leave a mark, the animal treatment apparatus being positioned within the marking portion hollow center and spaced apart from the absorbent pad containing the marking medium such that it is not in contact with the absorbent pad containing the marking medium;
   such that when the animal receives the treatment, no part of the animal treatment apparatus makes contact with the absorbent pad containing the marking medium, the marking portion marks the treatment location by stamping at the same time, the animal treatment being applied through the marking portion hollow center, and the mark surrounds, at a distance away from, the treatment location where the treatment was applied.

2. The apparatus of claim 1, wherein no additional movement or operation is required from an operator to stamp the mark over the movement or operation of treating the animal.

3. The apparatus of claim 1, wherein the marking portion also marks the location of where the treatment was applied.

4. The apparatus of claim 1, wherein the marking portion is circular and configured for leaving a circular mark on the animal.

5. The apparatus of 1, wherein the cassette is removably replaceable when the absorbent pad is exhausted.

6. The apparatus of claim 1, wherein there is an offset bracket to attach to the mount and to which the mounting portion can attach to offset the marking portion when the animal treatment is applied outside the periphery of the marking portion.

7. The apparatus of claim 1, wherein the applicator comprises a needle and further wherein the cassette acts as the guard that completely covers the needle, and which operatively uncovers the needle when the animal treatment apparatus is applied to the surface of the animal.

8. The apparatus of claim 1, wherein the applicator is selected from any of (a) a needle to apply subcutaneous treatment, (b) a spray for topical application to a surface layer, or (c) a spray that applies intraorifice to an oral, nasal, or other cavity.

9. An animal marking and treatment apparatus, comprising:
an animal treatment apparatus having an operative end with a treatment applicator portion, the animal treatment apparatus being configured to apply an animal treatment to a surface or subcutaneous layer at a treatment location of an animal via the treatment applicator portion; and
a marking portion located at the operative end of the animal treatment apparatus;
the marking portion is an absorbent pad containing a marking medium, held and presented within a cassette, and the cassette has a mounting portion, at an opposing end to that holding the absorbent pad, to cooperate with a mount on the operative end of the animal treatment apparatus;
the cassette being removably attachable to the animal treatment apparatus, and the cassette includes a removably replaceable cover for the absorbent pad to prevent the absorbent pad from drying out, wherein the removably replaceable cover has a proximal end and a distal end, the removably replaceable cover further having a hollow center which extends from the proximal end to and through the distal end;
the cassette when mounted to the operative end forms at least in part a guard over the treatment applicator portion at the operative end;
the marking portion having a hollow center corresponding at least in part with the hollow center of the removably replaceable cover and is configured to apply a mark;
the marking portion further surrounding and being separated from the treatment applicator portion, wherein the animal treatment apparatus is configured to apply the mark and the animal treatment at the same time, and further wherein, during use when applying the animal treatment, the marking portion remains surrounding and separated from the treatment applicator portion such that no part of the treatment applicator portion is in contact with the absorbent pad containing the marking medium, the animal treatment being applied through the marking portion hollow center; and
wherein when the animal treatment and the mark are applied to the animal, the mark surrounds, and is separated from, the treatment location.

10. The apparatus of claim 9, wherein the cassette forms the guard that covers and operatively uncovers the treatment applicator portion of the animal treatment apparatus.

11. The apparatus of claim 9, wherein the marking portion is shaped as a circular ring and configured for applying the marking as a circular ring marking on the animal.

12. The apparatus of claim 9, wherein the treatment applicator portion is selected from any of (a) a needle to apply subcutaneous treatment, (b) a spray for topical application to a surface layer, or (c) a spray that applies intraorifice to an oral, nasal, or other cavity.

13. An animal marking and treatment apparatus, comprising:
an animal treatment apparatus to apply an animal treatment to a surface or subcutaneous layer at a treatment location of an animal via an applicator at an operative end; and
a marking portion, attached to the animal treatment apparatus, and located at the operative end;
the marking portion being an absorbent pad containing a marking medium, held and presented within a cassette, the cassette having a mounting portion, at an opposing end to that holding the absorbent pad, to cooperate with a mount on the operative end of the animal treatment apparatus;
the cassette further being removably attachable to the animal treatment apparatus, and the cassette further including a removably replaceable cover for the absorbent pad to prevent the absorbent pad from drying out, wherein the removably replaceable cover has a proximal end and a distal end, the removably replaceable cover further having a hollow center which extends from the proximal end to and through the distal end;
the cassette when mounted to the operative end forms at least in part a guard over the applicator at the operative end;
wherein the marking portion has a marking portion hollow center corresponding at least in part with the hollow center of the removably replaceable cover and is configured to leave a mark, the animal treatment apparatus, during use when the animal receives the animal treatment, being positioned within the marking portion hollow center and spaced apart from the absorbent pad containing the marking medium such that it is not in contact with the absorbent pad containing the marking medium;
the applicator being configured to extend through the marking portion hollow center and to be separated from the marking portion hollow center when the applicator extends through the marking portion;
such that when the animal receives the animal treatment, no part of the animal treatment apparatus makes contact with the absorbent pad containing the marking medium, the marking portion marks the treatment location by stamping the animal at the same time, the animal treatment being applied through the marking portion hollow center; and
wherein the mark surrounds, at a distance away from, the treatment location where the animal treatment was applied.

* * * * *